United States Patent
Simonson

(10) Patent No.: US 6,841,159 B2
(45) Date of Patent: Jan. 11, 2005

(54) **RAPID LATERAL FLOW ASSAY FOR DETERMINING EXPOSURE TO *MYCOBACTERIUM TUBERCULOSIS* AND OTHER MYCOBACTERIA**

(75) Inventor: Lloyd G. Simonson, Spring Grove, IL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 12 days.

(21) Appl. No.: 10/061,036

(22) Filed: Jan. 30, 2002

(65) Prior Publication Data

US 2003/0143652 A1 Jul. 31, 2003

(51) Int. Cl.⁷ ........................... A61K 39/04; A61K 9/02
(52) U.S. Cl. ............................... 424/248.1; 424/130.1; 424/164.1; 424/168.1; 424/184.1; 424/234.1; 435/4; 435/7.1; 435/7.32
(58) Field of Search ........................ 424/130.1, 164.1, 424/168.1, 184.1, 234.1, 248.1; 435/4, 7.1, 7.32

(56) References Cited

U.S. PATENT DOCUMENTS

| | | | |
|---|---|---|---|
| 4,268,434 A | | 5/1981 | Higerd et al. |
| 4,391,904 A | * | 7/1983 | Litman et al. ............. 435/7.91 |
| 4,458,014 A | | 7/1984 | Ebersole |
| 4,639,419 A | | 1/1987 | Olsen et al. |
| 4,866,167 A | | 9/1989 | Chen et al. |
| 4,965,192 A | | 10/1990 | Maes |
| 5,830,410 A | | 11/1998 | Thieme et al. |
| 5,922,614 A | | 7/1999 | Cesarczyk |
| 6,548,309 B1 | | 4/2003 | Moore et al. |

OTHER PUBLICATIONS

R. A. Cole, et al., "Clinical Evaluation of a rapid immunochromatographic Assay Based on the 38 kDa antigen of *Mycobacterium tuberculosis* on Patients with Pulmonary Tuberculosis in China"; Tubercle and Lung Disease (1996) 77, p 363–368.
Sudha Pottumarthy et al., "A Comparison of Seven Tests for Serological Diagnosis of Tuberculosis"; Journal of Clinical Microbiology, Jun. 2000, p. 2227–2231.
J.R. Reddy et al., "An immunochromatographic serological assay for the diagnosis of *Mycobacterium tuberculosis*"; Comparative Immunology, Microbiology & Infectious Diseases 25 (2002) 21–27.
Web site: (http://home.hkstar.com/~granttec/news.html); "New Serum Test for Tuberculosis", 1 sheet.
Web site: (http://www.omegadiagnostics.com.uk); "Products", "The Company", "TB Disease Background", "TB Diagnostic Techniques", "TB Role of TB Serology", "TB Potential serological applications using 38/16 kDa antigen", "TB Questions and Answer"; 9 sheets.

Wilkinson R.J., Haslov, K., Rappuoli, R., Giovannoni, F., Narayanan, P.R., Desai, C.R., Vordermeier, H.M., Paulsen, J., Pasvol, G., Ivanyi, J., and Singh, M. Evaluation of the recombinant 38–kilodalton antigen of *Mycobacterium tuberculosis* as a potential immunodiagnostic reagent. *J. Clin. Microbiol.* 35(3): 553–7. Mar 1997.
Maekura, R., Nakagawa, M., Nakamura, Y., Hiraga, T., Yamamura, Y., Ito, M., Ueda, E., Yano, S., He, H., Oka, S., et al. Clinical evaluation of rapid serodiagnosis of pulmonary tuberculosis by ELISA with cord factor (trehalose–6, 6'–dimycolate) as antigen purified from *Mycobacterium tuberculosis*. *Am. Rev. Respir. Dis.* 148:997–1001.Oct, 1993.
Young, D., Kent, L., Rees, A., Lamb, J., and Ivanyi, J. Immunological activity of a 38–kilodalton protein purified from *Mycobacterium tuberculosis*. *Infect. Immun.* 54(1): 177–83. Oct, 1986.
Singh, M., Andersen, A.B., McCarthy, J.E., Rohde, M., Schutte, H., Sanders, E., and Timmis, K.N. The *Mycobacterium tuberculosis* 38–kDa antigen: overproduction in *Escherichia coli*, purification and characterization. *Gene* 117(1): 53–60. Aug. 1992.
Rosales–Borjas, D.M., Zambrano–Villa, S., Elinos, M., Kasem, H., Osuna, A., Mancilla, R., and Ortiz–Ortiz, L. Rapid screening test for tuberculosis using a 38–kDa antigen from *Mycobacterium tuberculosis*. *J. Clin. Lab. Anal.* 12 (2): 126–9. 1998.
Bassey, E.O.E., Catty, D., Kumararatne, D.S., and Raykundalia, C. Candidate antigens for improved serodiagnosis of tuberculosis. *Tubercle Lung Dis.* 77:136–145. 1996.

(List continued on next page.)

Primary Examiner—Rodney P Swartz
(74) Attorney, Agent, or Firm—Joseph K. Hemby, Jr.

(57) ABSTRACT

An assay method and kit is disclosed for detecting the presence of at least one predesignated, target antibody to a mycobacterium in a sample selected from one or more patient bodily fluids. The method comprises the following steps: (a) contacting the sample of one or more patient bodily fluids with at least one mycobacterium antigen on a lateral-flow assay membrane to bind to the target antibody in the sample; (b) previously, simultaneously or subsequently to step (a), binding the at least one mycobacterium antigen with a conjugated label producing a detectable signal; and (c) detecting the signal whereby the presence of the target antibody is determined in the sample by the intensity or presence of the signal. The method can further comprise the step of evaluating immunization status of the patient from whom the sample came by comparing the signal or lack thereof with immunizations previously received by the patient and in comparison to a known standard control. In a preferred embodiment, the mycobacterium antigen specifically binds to *Mycobacterium tuberculosis* specific antibodies. Preferably, the immunoassay of the present invention comprises a lateral-flow assay comprising a membrane, a conjugated label pad, and at least one mycobacterium antigen bound to the membrane. In a preferred embodiment, the at least one mycobacterium antigen is selected from the group consisting of 38 kDa and 16 kDa antigens.

29 Claims, 3 Drawing Sheets

OTHER PUBLICATIONS

Kadival, G.V., Chaparas, S.D., and Hussong, D. Characterization of serologic and cell–mediated reactivity of a 38–kDa antigen isolated from *Mycobacterium tuberculosis*. *J. Immunol.* 139(7): 2447–51. Oct, 1987, (abstract only).

Fujiwara, N., Pan, J., Enomoto, K., Terano, Y., Honda, T., and Yano, I. Production and partial characterization of anti–cord factor (trehalose– 6,6'–dimycolate) IgG antibody in rabbits recognizing mycolic acid subclasses of *Mycobacterium tuberculosis* or *Mycobacterium avium*. *FEMS Immunol. Med. Microbiol.* 24(2): 141–9. Jun, 1999.

He, H., Oka, S., Han, Y.K., Yamamura, Y., Kusunose, E., Kusunose, M., and Yano, I. Rapid serodiagnosis of human mycobacteriosis by ELISA using cord factor (trehalose– 6, 6'–dimycolate) purified from *Mycobacterium tuberculosis* as antigen. *FEMS Microbiol. Immunol.* 3(4): 201–4. Aug, 1991.

Enomoto, K., Oka, S., Fujiwara, N., Okamoto, T., Okuda, Y., Maekura, R., Kuroki, T., and Yano, I. Rapid serodiagnosis of *Mycobacterium avium–intracellulare* complex infection by ELISA with cord factor (trehalose 6, 6'–dimycolate), and serotyping using the glycopeptidolipid antigen. *Microbiol. Immunol.* 42(10): 689–96.1998.

Chang, Z., Primm, T.P., Jakana, J., Lee, I.H., Serysheva, I., Chiu, W., Gilbert, F., and Quiocho, F.A. *Mycobacterium tuberculosis* 16–kDa antigen (Hsp 16.3) functions as an oligomeric structure in vitro to suppress thermal aggregation. *J. Biol. Chem.* 271:7218–7223. 1996.

Cunningham, A.F., and Spreadbury, C.L. Mycobacterial stationary phase induced by low oxygen tension:cell wall thickening and localization of the 16–kilodalton alpha–crystalline homolog. *J. Bacteriol.* 180(4): 801–8. Feb, 1998.

* cited by examiner

Sample is added to well at left and flow is from left to right.
Positive TB Reaction (top) = Red stripes in both the $T_1$ (38 and 16 kDa Antigen mix)(and usually $T_2$) and Control (C) positions.
Positive Mycobacteria (non-TB) (middle) = Red stripe at $T_2$ and C positions.
Negative Reaction(bottom) = Red stripe only in C position. The C must always be positive or the test is invalid.

RAPID LATERAL FLOW ASSAY FOR DETERMINING EXPOSURE TO *MYCOBACTERIUM TUBERCULOSIS* AND OTHER MYCOBACTERIA

STATEMENT REGARDING FEDERALLY SPONSORED RESEARCH OR DEVELOPMENT

The invention was made by the U.S. Navy, an agency of the United States Government. The U.S. Government has a paid-up license in this invention.

BACKGROUND OF THE INVENTION

1. Field of the Invention

The present invention relates to a rapid test method and assay for determining the presence of antibodies in a patient to disease-related antigens, e.g., antibodies to *Mycobacterium tuberculosis,* and other mycobacterial antigens.

2. Description of the Related Art

Antibodies are naturally produced biomolecules that react specifically with usually foreign biomolecules called antigens. Disease-related microbial infections, e.g., *Mycobacterium tuberculosis,* which causes tuberculosis (TB), are usually characterized by the production of antibodies to the specific disease-related antigens. Antibodies are also produced with other diseases and afflictions, e.g., autoimmune diseases, wherein there is often a destructive antibody response to the host. In the case of autoimmune diseases, the host supplies the disease-related antigen, a host tissue. In this case, the corresponding host antibody synthesis may have been initiated by either a foreign substance or by a host tissue not normally encountered by the host's immune system. Subsequent antibody production may proceed in the absence of the foreign substance, due to similar structural nature of the host tissue. Herein the term "disease-related antigen" includes microbial antigens and antigens associated with the host antibody response in autoimmune diseases.

Infectious diseases are widespread in the world. Military personnel, including Navy and Marine personnel, are at particular risk because of their global deployment. According to the World Health Organization, the infectious disease tuberculosis caused by *Mycobacterium tuberculosis* (MTB) kills about three million people every year.

There are several conventional tests for MTB, however these conventional tests all have disadvantages.

One conventional test is a purified protein derivative (PPD) skin test. In this test, a PPD is injected subcutaneously into a patient, and after 2 to 3 days, the site of injection is observed to determine whether there is hardening and/or discoloration of the patient's skin. This test is believed to be only about 50–75% accurate. In persons that have been immunized with *Mycobacterium bovis* BCG, there are a high percentage of false positives. Another disadvantage of the PPD skin test is that it requires a needle injection, and patient compliance is low in coming back for observation by trained medical personnel for hardening and/or discoloration. This test is typically used as a screening test for people who do not have symptoms of tuberculosis. The specificity of purified protein derivative (PPD) skin test for the detection of tuberculosis infection is compromised by exposure to environmental mycobacteria. Wilkinson R. J., Haslov, K., Rappuoli, R., Giovannoni, F., Narayanan, P. R., Desai, C. R., Vordermeier, H. M., Paulsen, J., Pasvol, G., Ivanyi, J., and Singh, M. Evaluation of the recombinant 38-kilodalton antigen of *Mycobacterium tuberculosis* as a potential immunodiagnostic reagent. *J. Clin. Microbiol.* 35(3): 553–7. March 1997.

Another conventional test is a culture test. However, this test takes up to 6 to 8 weeks since that is how long it takes for the MTB organism to grow to an amount that is visibly detectable. Another disadvantage of the culture test is that typically only about half of all samples wherein the *Mycobacterium tuberculosis* is present actually grow to the point where it is detectable. Thus, this method has about 50% false negatives.

Another conventional test is a chest x-ray. However, this method does not work if the person undergoing the chest x-ray has been recently infected with *Mycobacterium tuberculosis*. Another disadvantage is that the chest x-ray can be mis-read. Other disadvantages are the cost of the x-ray and need to subject a person to x-rays.

Another conventional test is an acid fast staining test. This method detects the most infectious patients but not those with extrapulmonary disease. In this method, patient sputum (i.e., coughed up phlegm) is smeared onto a glass slide, and a microscopic chemical stain for acid fast bacilli (AFB) is performed using the Ziehl Nielson method. The sample is then viewed under a microscope for the presence of the red staining acid-fast mycobacterium organisms. This test requires hours to complete and a high level of expertise of the microbiologist running the test. Only after sputum tests on three separate occasions have come up negative is the patient considered negative for AFB. Examination of three sputum samples detects up to 87% of pulmonary tuberculosis patients, but a considerably lower percentage of patients (43%) with extrapulmonary disease.

Another test is a MycoDot test. The MycoDot test detects anti-lipoarabinomannan IgG antibodies in serum/whole blood to diagnose cases of active TB. The MycoDot test employs the lipoarabinomannan (LAM) antigen bound to plastic combs. During incubation of the comb in the diluted serum sample for 6 minutes, the free anti-LAM antibodies, if present in the serum/blood of the individual, will bind to the antigen on the comb. Next, the excess antibodies that might be loosely attached to the comb are washed off. During incubation of the comb in a colloidal gold signal reagent for 10 minutes, the bound anti-LAM antibodies on the comb, if present, then bind to the protein ligand attached to the gold particles, providing a pink colored aggregate at the antigen spot on the comb. Next, any excess signal reagent is washed off the comb. The presence of a pink colored spot on the comb, generated as a result of the steps described above, is indicative of a positive reaction due to active TB. However, the test requires either serum or blood and takes at least 20 minutes to perform. It is also not a portable test and requires a laboratory facility to perform.

Several mycobacterial antigens are presently being exploited in the development of improved vaccines and serodiagnostic reagents. A 38-kDa antigen of *Mycobacterium tuberculosis* was evaluated as a potential immunodiagnostic reagent. Wilkinson R. J., Haslov, K., Rappuoli, R., Giovannoni, F., Narayanan. P. R., Desai, C. R., Vordermeier, H. M., Paulsen, J., Pasvol, G., Ivanyi, J., and Singh, M. Evaluation of the recombinant 38-kilodalton antigen of *Mycobacterium tuberculosis* as a potential immunodiagnostic reagent. *J. Clin. Microbiol.* 35(3): 553–7. March 1997. More specifically, serological tests pursuant to this method found a 72.6% sensitivity of the test in comparison with that of culture, and the specificity was reported as 94.9%.

Young et al. (3) reported that the 38 kDa antigen carries two non-overlapping epitopes, recognized by monoclonal antibodies TB71 and TB72, respectively, that are expressed substantially more strongly by MTB than by *Mycobacterium*

*bovis*. Antibodies were detected in sera from tuberculosis patients estimated by competition binding against TB72 antibody using a 38-kDa-antigen-coated microtiter plates. Their results suggest the immunodominance of the species-specific B cell and cross-reactive T-cell stimulatory epitopes.

Singh et al. (4) also conclude the 38-kDa protein (Ag38) is an immunodominant antigen of potential utility for diagnosis and vaccine development. The recombinant antigen that they produced could not be distinguished antigenically from the native protein of MTB.

A screening test was described by Rosales-Borjas (5) for the diagnosis of tuberculosis (TB) by immunodot (IDt) using the 38-kDa glycoprotein antigen, which has shown great specificity in their previous serologic analyses. The serologic test was used to examine 28 sera from patients with lung tuberculosis. Of these, 85% were positive by micro-ELISA and by the IDt test described. Control sera from healthy subjects (n=20) gave negative results for ELISA and for IDt, which indicated that their screening test was highly specific. However, the sample application required a 30-minute soaking procedure followed by drying and two additional 10 minute incubation procedures plus numerous washing procedures. It also requires a laboratory facility and skilled personnel to perform.

Bassey et al. (6) provide evidence that a combination of MTB antigens may be a useful basis for developing a diagnostic antibody test.

Kadival et al. stated that the 38-kDa antigen appears to be conserved (7) and is only found in MTB and *M. bovis* BCG. They also observed the 38-kDa antigen may contain a specific epitope detected by serology, and also contains epitopes that are cross-reactive for cellular immunity. Unlike the 38 kDa antigen, cord factor (trehalose-6,6'-dimycolate) (TDM) has been used as a somewhat less specific antigenic marker for several mycobacteria (2, 7–10). Maekura et al. and Fujiwara et al. (2 and 8) describe ELISA procedures with TDM that are useful for the serodiagnosis of tuberculosis.

Patients with active pulmonary tuberculosis showed significantly higher titers of IgG antibodies against cord factor (TDM) than did other groups (p<0.001)(2). The ELISA had a sensitivity of 81% and a specificity of 96%. From these results, it was concluded that the detection of IgG antibodies against TDM is useful for serodiagnosis of active pulmonary tuberculosis. It also indicated that the anticord factor antibody titers decline to the normal level as a result of antituberculosis chemotherapy making TDM a possible prognostic marker.

He et al. (9) also developed an ELISA using TDM and found the sensitivity and specificity to be 83.8% and 100%, respectively. They concluded that ELISA with TDM as the antigen is simple, reproducible, and useful for the rapid serodiagnosis of general mycobacterial infections including tuberculosis.

Enomoto et al. (10) state that *Mycobacterium avium-intracellulare* complex (MAC) is one of the most important opportunistic pathogens, particularly in patients with acquired immunodeficiency syndrome (AIDS). Their findings suggest that ELISA using TDM is useful for rapid serodiagnosis of MAC infection.

Chang et al. (11) have expressed and purified the 16-kDa antigen from MTB, and characterize it as an immunodominant antigen with serodiagnostic value. Cunningham et al. (12) feel that the 16-kDa protein may be a marker for the dormant (latent) state of TB.

U.S. Pat. No. 4,458,014 discloses a SEROLOGICAL METHOD FOR THE IDENTIFICATION OF MICROORGANISMS for the identification of diseases of the mouth. U.S. Pat. No. 4,866,167 discloses a DETECTION OF PATIENT ORAL CELLS BY NUCLEIC ACID HYBRIDIZATION to detect oral bacterial species. The methods of both of these patents are technically complex, time consuming and are not rapid.

U.S. Pat. No. 4,639,419 discloses an IMMUNOLOGICAL COLOR CHANGE TEST INVOLVING TWO DIFFERENTLY COLORED REAGENT SPOTS. This patent discloses an agglutination reaction directed toward identifying antigenic material wherein a colored substrate and colored reagent combine, in positive reactions, to give the appearance of a third color.

There are several screening tests for tuberculosis. The Mantoux test uses tuberculin purified protein derivative (PPD) which is injected intracutaneously (e.g., Tubersol®, Connaught Laboratories Limited, Willowdale, Ontario, Canada). A delayed hypersensitivity reaction develops in individuals having previous exposure to *Mycobacterium tuberculosis*. The injection site is normally read within 48 to 72 hours after intracutaneous injection of the antigen; a palpable induration measuring 10 mm in diameter or more is considered a positive reaction. This procedure is accepted as an aid in the diagnosis of tuberculosis infection.

The Heaf test uses a multiple puncture disk which introduces needles through concentrated Old Tuberculin applied to the skin. The tine test uses tuberculin adhering to metal tines which is then inoculated by simple pressure into the skin. The Heaf and tine tests are acceptable for screening but should be confirmed by the Mantoux test. Antigenic material can also be applied by scratch, i.e., Pirquet's test. Similar to the Mantoux test, these invasive tests generally require 48 to 72 hours after inoculation before results can be determined. The Bacillus of Calmette and Guerin (BCG) is a live, attenuated strain of *Mycobacterium bovis* which has been used with varying success as a vaccine against tuberculosis in countries where the prevalence of tuberculosis is high. BCG causes tuberculin conversion to positive; it has also been used to stimulate the immune system against a variety of medical conditions. Both PPD and BCG can serve as suitable antigens to detect general mycobacterial infections with this method.

Other antigens have been described. Maes has described A60-ANTIGEN FROM MYCOBACTERIA AND USE THEREOF AS TUBERCULIN VACCINE in U.S. Pat. No. 4,965,192. This patent describes the A60-antigen as being effective for detecting prior exposure of an individual to Mycobacterial infections through the use of a cutaneous test. This patent is similar to other invasive inoculation tests mentioned earlier except that a new antigen is used and 24 to 48 hours are required to observe the responses at the test site.

To summarize, the conventional serological methods do not provide a non-invasive, rapid diagnostic test that measures exposure to mycobacteria, including MTB. A simple, rapid and non-invasive screening method would be especially useful in evaluating MTB exposure, such as for sailors and marines returning from endemic areas.

BRIEF SUMMARY OF THE INVENTION

The immunoassay method and kit of the present invention provides a rapid test to determine previous exposure of individuals to MTB and/or other mycobateria, and thus aids in the diagnosis of infectious diseases due to such mycobacteria, including tuberculosis. The present invention can also be used to field screen local inhabitants of endemic areas and isolate positives from the general population.

More specifically, the present invention comprises a method for detecting the presence of at least one predesignated, target antibody to a mycobacterium in a sample selected from one or more patient bodily fluids which comprises the following steps: (a) contacting the sample of one or more patient bodily fluids with at least one mycobacterium antigen on a lateral-flow assay membrane to bind to the target antibody in the sample; (b) previously, simultaneously or subsequently to step (a), binding the at least one mycobacterial antigen with a conjugated label producing a detectable signal; and (c) detecting the signal whereby the presence of the target antibody is determined in the sample by the intensity or presence of the signal.

In accordance with the present invention, the one or more bodily fluids is selected from the group consisting of saliva, oral rinse expectorant, oral fluid including oral mucosal transudate and gingival crevicular fluid, urine, sweat, tears, blood, serum, stool, gastric fluid, synovial fluid, phlegm, culture media and other clinical and laboratory specimens and samples. In a preferred embodiment of the invention, the one or more bodily fluids used in the method is saliva or diluted serum.

The present invention further provides the step of evaluating immunization status of the patient from whom the sample came by comparing the signal or lack thereof with immunizations previously received by the patient and in comparison to a known standard control.

In a preferred method, the antigen specifically binds to MTB specific antibodies.

The invention also provides an immunoassay kit for detecting a pre-designated target antibody or antibodies to a mycobacterium in a sample selected from one or more patient bodily fluids which comprises: (a) a lateral-flow assay comprising a membrane, (b) a conjugated label pad, and (c) at least one mycobacterium antigen bound to the membrane. In a preferred kit, the at least one mycobacterium antigen specifically binds to MTB specific antibodies. In a preferred kit, the at least one mycobacterium comprises two or more mycobacterial antigens. In a preferred embodiment, the conjugated label pad comprises Protein A conjugated with colloidal gold.

In a preferred embodiment, the sample is placed on a sample pad. The sample filters down through the sample pad and then through a conjugate label pad containing a conjugate label, e.g., Protein A conjugated with colloidal gold. The gold particles serve as an indicator dye. The conjugate label binds to IgG antibodies in the sample to form complexes, and the complexes then migrate along the membrane or detection strip. The complexes of MTB specific IgG antibodies, if present, bind to the at least one mycobacterium antigen that is immobilized in a discreet location on the membrane. Formation of this gold-labeled Protein A antibody complex with its mycobacterial antigen results in a detectable colored line, indicating a positive result that MTB specific antibodies are present in the sample. The time for this test is about 5–10 minutes, and under 20 minutes.

The results can be used to evaluate immunization status of a patient. For example, if the sample tests positive, and the sample came from a person who has received a TB vaccine, then the positive result will indicate that the appropriate immune response was elicited from that person, particularly if there are no other indications or symptoms of TB in the person. If the sample tests negative, and the sample came from a person who has received a TB vaccine, then the negative result will indicate that the person has not been properly immunized.

Thus, the immunoassays of the present invention provide markers of vaccine status by detecting specific MTB antibodies in patient bodily fluids, such as saliva. This approach has widespread future potential for monitoring exposure to toxins or disease and for assessing immunization status against various infectious diseases, including TB. Possible long-term applications of this hand-held, diagnostic tool include continuing field surveillance of vaccinated personnel to verify protective immunization and to assist in the determination of the optimum dose schedule for TB vaccine administrations. This test method may also be employed to monitor personnel and to follow the progression and treatment of TB and can be applied to other infectious diseases for which specific antigen and antibodies are known.

The present invention is particularly useful as a rapid, non-invasive diagnostic tool to assess MTB exposure or TB immunization status of military personnel. The hand-held, in vitro test method of the present invention that can be administered by minimally trained personnel is designed for field use in forward-deployed areas. The present invention provides an immunoassay that will serve as a marker of vaccine status to assess the level of protective antibodies. Applications of this test method may also provide useful data to determine the optimum number of doses and schedule for MTB vaccinations. This could be accomplished by following the progression of antibody response at each stage of a TB vaccination series. By monitoring antibody titer, it can be determined: (1) If a particular injection series is needed for vaccine effectiveness; (2) If annual boosters are required to maintain protective immunization, or alternatively, how long TB immunization lasts; and (3) The point in the injection series at which maximum antibody titer is achieved. It is not possible to conduct research to directly determine patient vaccine effectiveness against the MTB. However, protection of non-patient primates with the MTB vaccine has been demonstrated in a number of laboratories and continues to provide the best supportive evidence of its efficacy.

The present invention can also be used to verify the exposure to a biowarfare agent, such as MTB, in a patient. For example, if the sample testing positive came from a patient who has not been vaccinated against the biowarfare agent, then the positive test indicates exposure to the biowarfare agent in the patient, and treatment against the biowarfare agent should begin immediately. Detection of Immunoglobulin M (IgM) or other immunoglobulins (other than IgG) may be more appropriate in this use and certain other uses.

In accordance with the present invention, rapid lateral flow devices can be configured with a combination of striped antigens that will simultaneously determine exposure to both specific (MTB and *M. bovis*) and general shared mycobacterial antigens.

In accordance with the present invention, BCG can serve as a source of suitable antigens to detect general mycobacterial infections.

DETAILED DESCRIPTION OF THE INVENTION

Figure 1:
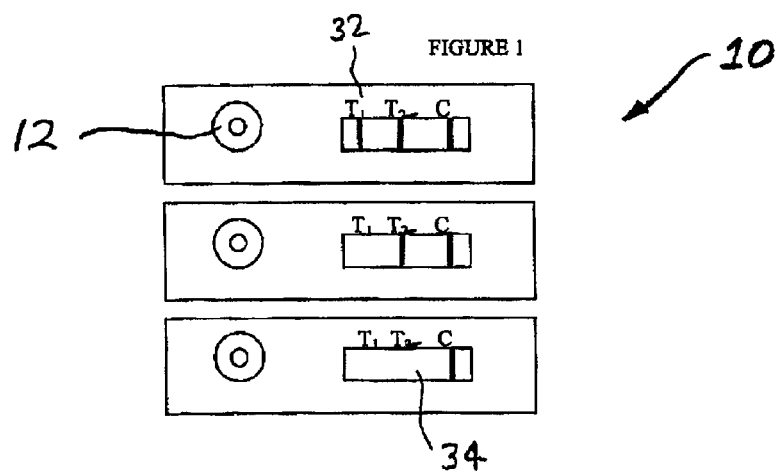
FIG. 1 shows a top view of a preferred embodiment of the present invention.
Figure 2:
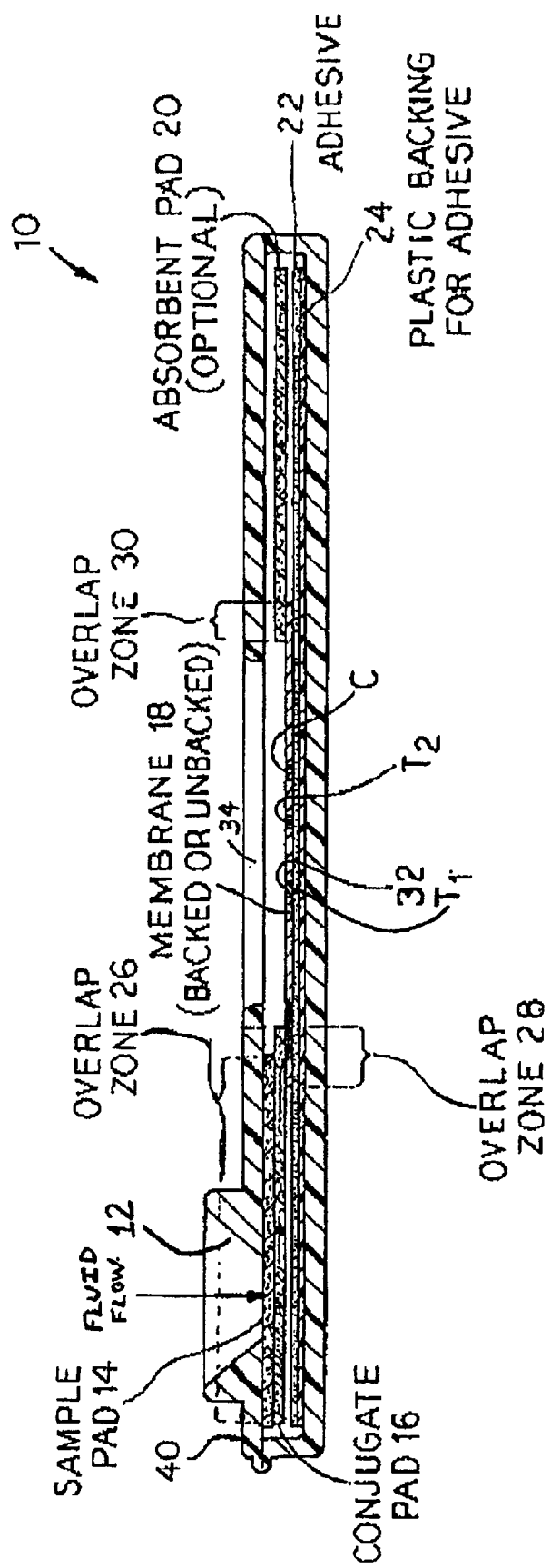
FIG. 2 shows a side view of the preferred embodiment shown in FIG. 1.

As shown in FIGS. 1 and 2, a preferred immunoassay 10 of the present invention, comprises a sample well 12, a sample pad 14, a conjugate label pad 16, a lateral-flow assay membrane or detection strip 18, an absorbent pad 20, an adhesive layer 22, a plastic backing 24, and a plastic housing 40. Sample pad 14 overlaps with conjugate label pad 16 to form a first overlap zone 26. Conjugate label pad 16 and membrane 18 form a second overlay zone 28. Membrane 18 and Absorbent pad 20 form a third overlap zone 30. A body fluid specimen (not shown) can be placed in sample well 12 and filters down through the sample pad 14 and then through a conjugate label pad 16 containing a conjugate label, e.g., Protein A conjugated with colloidal gold. The gold particles, preferably having a diameter size in the range of about 20–55 nm, and more preferably in the range of about 40–45 nm, serve as an indicator dye. The conjugate label binds to antibodies in the sample to form a complex, and the complex then migrates along the membrane 18.

In a preferred embodiment, MTB specific antibodies bind to a mixture of at least two antigens that are immobilized in a discrete location 32 on membrane 18. Formation of this antigen mixture-antibody complex causes the indicator dye to precipitate and form a detectable colored red line (illustrated as "$T_1$" in FIG. 1), indicating a positive result that MTB specific antibodies are present in the sample. FIG. 2 is an illustration of a test strip from Millipore Corporation (see Mansfield, M. (1999) A Short Guide: Developing Immunochromatographic Test Strips, Millipore Corporation, Bedford, Mass.) that has been modified in accordance with the present invention.

In a preferred embodiment, the mixture of at least two antigens comprises two antigen proteins, the 38 kDa (also known as antigen 5, antigen 78, Pab, and PhoS) and the 16 kDa antigens. Recombinant proteins of the 38 kDa, 16 kDa, ESAT-6, or CFP-10 may also be used instead of MTB culture products.

An assay is recorded as positive when a distinct band of the antigen mixture ($T_1$ on the assay 10 in FIG. 1) appears in addition to the control band. A control line (C) of Protein A will also form whether the antigen mixture line is colored or not, indicating the test is functioning properly. A negative test results when only the control (C) band appears in the membrane window. Preferably, each lateral-flow device is individually packaged in a plastic-lined foil pouch with a desiccant pad to ensure stability. These testing devices can be stored long-term (more than 6 months) at room temperature with no loss of activity.

The testing device can comprise a mixture of 0.72 or 1.8 $\mu$g recombinant 38 kDa and 16 kDa antigen proteins and/or other antigens such as ESAT-6, MPT-63, CFP-10, TB23 HYT6, F29.47, 21-2H3, MPT40 and others, immobilized on nitrocellulose strips as the test indicator ($T_1$) and Protein A as the control band (C). Since the 38 kDa and the 16 kDa antigen proteins are only found in MTB, a positive test is a highly specific indicator for MTB exposure.

Figure 3:
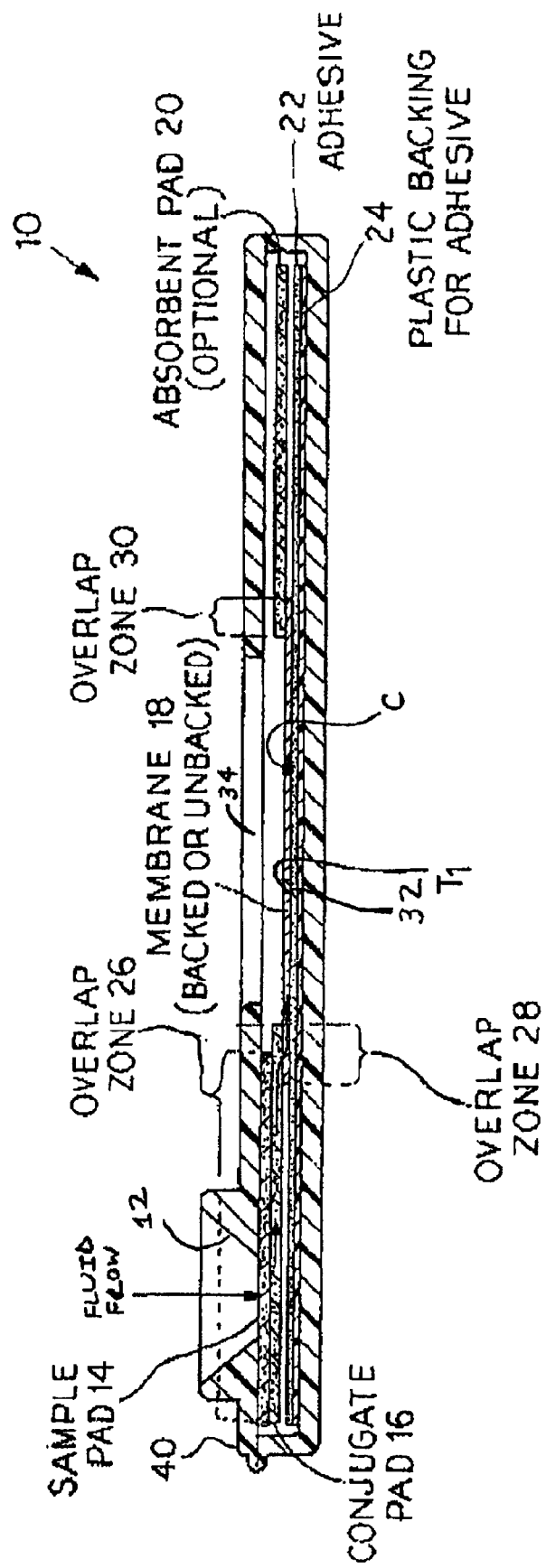
FIG. 3 shows a side view of an alternative embodiment of the present invention.

In a preferred embodiment, the assay 10 of the present invention can have a single test stripe ($T_1$). As shown in FIGS. 1 and 2, the assay 10 of the present invention can further comprise a second test stripe $T_2$, which can be located between $T_1$ and the control stripe C. In a preferred embodiment, the second test stripe $T_2$ can comprise an antigen mixture of shared common mycobacterial antigens (such as P32 of *M. bovis*, 65 or 64 kDa BCG antigen, MPB57 or BCG-a, LAM, and others), and stripe $T_1$ can be comprised of 16 kDa protein only as a measure of latent TB. While two test stripes $T_1$ and $T_2$ are shown in FIGS. 1 and 2, as noted above, assay 10 can have a single test stripe, as shown in FIG. 3. In accordance with the present invention, assay 10 can comprise more than two stripes to test for the presence of additional targeted antibodies in a sample selected from one or more patient bodily fluids.

Experience with saliva sample testing has shown that 4 drops of saliva and/or oral mucosal transudate and gingival crevicular fluid mixed with 2 drops of buffer, as added by bulb-pipette, work best for obtaining optimum results. This amount provides sufficient testing volume, and subsequent capillary flow pressure, to ensure optimum membrane flow rate as the sample migrates the entire length of the membrane. Calibration of several plastic, bulb-pipette medicine droppers that are used to add sample to the device indicates that each drop consists of about 40–50 $\mu$L volume. Therefore, 4 drops or 160–200 $\mu$L sample volumes can be used for each test. Four drops (160–200 $\mu$L) of stimulated saliva mixed with 2 drops (80–100 $\mu$L) of protease inhibitor/EDTA dilution buffer also appears to facilitate sample flow.

In a preferred embodiment, the time for this test is about 5–10 minutes, and under 20 minutes. The results can be used to evaluate immunization status of a patient. For example if the sample came from a person who has received an TB vaccine, then the positive result will indicate that the appropriate immune response was elicited from that person, particularly if there are no other indications or symptoms of TB in the person. If the sample tests negative, and the sample came from a person who has received a TB vaccine, then the negative result will indicate that the person has not been properly immunized.

If the sample tests positive, and the sample came from a person who has not received a TB vaccine, then the positive result will indicate that the person has been exposed to MTB. If the sample tests negative, and the sample came from a person who has not received a TB vaccine, then the negative result will indicate that the person has not been exposed to MTB, particularly if there are no other indications or symptoms of TB in the patient.

Membrane 18 can comprise any suitable material, e.g., a uniform-sized (10×500 mm) nitrocellulose membrane (Millipore™ XA3J072100). Conjugate label pad 16 can contain any suitable marker, e.g., dried colloidal gold-labeled Protein A as marker (see FIGS. 1 and 2) and be placed at one end of membrane 18. An absorption pad 20 is located at the opposite end of the membrane 18 and serves to draw the sample, e.g., saliva, along the membrane 18 by capillary action. A plastic backing 24 provides support for the adhesive layer 22 and membrane 18, and the combination can be cut into individual test strips (e.g., 5×60 mm) and fitted into a plastic housing. A round sample application well 12 is positioned directly above and in fluid communication with the sample pad 14, and a rectangular detection window 34 is located above the nitrocellulose membrane 18.

Thus, the present invention provides a rapid, simple, immunoassay test (two versions 1=non-invasive using saliva, and 2=invasive using diluted serum) for tuberculosis. The present invention provides a rapid test method for simultaneously determining the presence of antibodies in saliva (or serum) to *Mycobacterium tuberculosis* (MTB) and other mycobacteria. The method is fast (usually 5 minutes or less) and technically easy to perform. Maekura et al. (3) noted that the antibody titers to a mycobacterial antigen declined to normal levels as a result of antituberculosis chemotherapy. Therefore, an additional objective of the invention is to monitor prognosis following conventional MTB antibiotic therapy.

The rapid lateral flow devices of the present invention comprise a combination of striped antigens that will simultaneously determine exposure to both specific (MTB and *M. bovis*) and general mycobacterial antigens. The present invention provides a salivary diagnostic method and assay to supplant and/or complement invasive procedures such as the PPD skin test and their corresponding slow and labor intensive methods. Using saliva or sera in accordance with the immunoassay of the present invention would aid in the diagnosis of tuberculosis. Using saliva as a source of specific antibodies directed at TB-related antigens is a new and unique technological approach in the diagnosis of TB.

The method of the present invention preferably tests either saliva specimens or diluted serum. Saliva is preferred as the antibody source since whole saliva is the most easily collected of available specimens and generally mirrors serum antibody contents. Pre-filtered or unfiltered saliva may be used. If patient serum is used, a loopful (5 $\mu$L) can be diluted with 6 drops (240–300 $\mu$L) of a diluent and will be aliquoted and mixed with the diluent. The diluted sample can be added dropwise to a lateral-flow device using a transfer pipette. Either a single test stripe or at least two antigen test stripes in addition to a positive control stripe can be present in the device.

Salivary samples and serum can be collected from patients known to be infected with MTB according to positive culture results, AF staining and radiographic results. The lateral flow device test concentrations are optimized by setting sensitivity thresholds using positive clinical samples and known negative controls.

A patient sample can be added to the sample well. A pad containing Protein A colloidal gold comes in contact with the flowing sample. As the samples flow from the application spot, the first test stripe can contain a single antigen or a mixture of two or more antigens (e.g., the 38 kDa plus the 16 kDa antigens)(recombinant proteins may be used instead of MTB culture products). Since these antigens are only found in *M. tuberculosis*, a positive result is highly specific for MTB exposure. The second stripe (if present) encountered by the flowing sample will contain either a single antigen or a mixture of non-specific mycobacterial antigens. In other words, the second stripe can comprise a shared mycobacterial antigen common to all mycobacteria or a mixture of such antigens.

It is believed that the position of the two test stripes is important. If the second stripe is positive, it indicates that the patient has been exposed to any mycobacteria (including MTB) or has sero-converted in response to PPD skin tests. The patient sample antibodies first bind by their Fragment crystallizable (Fc) portion to the Protein-A colloidal gold label reagent. A positive result is visualized as a red stripe, which indicates where an antigen antibody reaction has occurred and has complexed along with the Protein-A-colloidal gold label (or other suitable label). If the second stripe only is positive, the patient has been exposed to a non-MTB mycobacterium. If both test stripes are positive, or only the first test stripe is positive, then the patient has been exposed or is still infected with MTB. The positive control (C) must be positive (red stripe) or the test is invalid. This control is accomplished by striping a material that will react with patient sample antibodies as they flow across the C position. Results from lateral flow saliva and serum tests are usually available in one to five minutes, and less than twenty minutes, including that from an internal positive control.

The method can further comprise the step of evaluating immunization status of the patient from whom the sample came by comparing the signal or lack thereof with immunizations previously received by the patient and in comparison to a known standard control.

The assay of the present invention is a rapid, sensitive and specific screening device. It can be suitable for field and shipboard use by ancillary medical personnel. No electrical equipment is required to perform the method of the present invention.

Sample Collection

According to a preferred embodiment, a polypropylene collection cup or container may be used. It is within the scope of the invention to use a pliable material for the container as described in column three of U.S. Pat. No. 5,922,614, which is expressly incorporated herein by reference thereto. Volunteers can be given a single piece of sugarless peppermint chewing gum and asked to chew for 30 seconds before collecting samples of stimulated saliva. Typically, volunteer subjects provide sample volumes of about 2–4 mL for unstimulated saliva, while a volume of 5–8 mL is most common after chewing a piece of gum. Alternatively, an absorbent element may be rubbed along the gum line for a short period of time, preferably up to thirty seconds, then the absorbent element may be held in place along the gums for a longer period of time, preferably up to two minutes. U.S. Pat. No. 5,830,410, which is expressly incorporated herein by reference thereto, more fully describes this method in columns six and seven and also describes a representative collection device in FIGS. 1A and 1B. The pliable material collection cup or container may be placed around the oral-fluid-saturated absorbent element and deformed or squeezed to extract the oral fluid. Each of these samples can be placed on ice immediately after collection to ensure stability.

Protease Inhibitor Solution

To preserve saliva samples for storage and biological assay in accordance with the present invention, a mycobacteriocidal protease inhibitor solution may sometimes be appropriate. For example, a general protease inhibitor cocktail (premade Sigma™ Protease Inhibitor Cocktail P2714) can be added to each sample 1:20 to prevent protein degradation from oral bacterial enzymes. These samples can then be returned to the laboratory for testing.

A protease inhibitor cocktail can be provided as 100× lyophilized powder. The protease inhibitor cocktail can be reconstituted to 10× with Barnstead Still quality water [10 ml]. TABLE of WORKING CONCENTRATIONS in Protease Inhibitor Solution EDTA 10 mM AEBSF 20 mM Bestatin 1300 $\mu$M E-64 14 $\mu$M Leupeptin 10 $\mu$M Aprotinin 3 $\mu$M At these working concentrations, the protease inhibitor solution can be diluted 10× for proteolytic inhibition.

The term patient used herein includes humans, as well as animals. Thus, the present invention can be used for diagnostics for veterinary tests.

Obviously, many modifications and variations of the present invention are possible in light of the above teaching. It is therefore to be understood that, within the scope of the appended claims, the invention may be practiced otherwise than as specifically described. The principles described above can be readily modified or adapted for various applications without departing from the generic concept, and therefore such adaptations and modifications are intended to be comprehended within the meaning and range of equivalents of the enclosed embodiments. It is to be understood that the terminology and phraseology herein is for the purpose of description and not of limitation.

Publications:

1. Wilkinson R. J., Haslov, K., Rappuoli, R., Giovannoni, F., Narayanan, P. R., Desai, C. R., Vordermeier, H. M., Paulsen, J., Pasvol, G., Ivanyi, J., and Singh, M. Evaluation of the recombinant 38-kilodalton antigen of *Mycobacterium tuberculosis* as a potential immunodiagnostic reagent. *J. Clin. Microbiol.* 35(3): 553–7. March 1997.
2. Maekura, R., Nakagawa, M., Nakamura, Y., Hiraga, T., Yamamura, Y., Ito, M., Ueda, E., Yano, S., He, H., Oka, S., et al. Clinical evaluation of rapid serodiagnosis of pulmonary tuberculosis by ELISA with cord factor (trehalose-6,6'-dimycolate) as antigen purified from *Mycobacterium tuberculosis*. *Am. Rev. Respir. Dis.* 148:997–1001. October 1993.
3. Young, D., Kent, L., Rees, A., Lamb, J., and Ivanyi, J. Immunological activity of a 38-kilodalton protein purified from *Mycobacterium tuberculosis*. *Infect. Immun.* 54(1): 177–83. October, 1986.
4. Singh, M., Andersen, A. B., McCarthy, J. E., Rohde, M., Schutte, H., Sanders, E., and Timmis, K. N. The *Mycobacterium tuberculosis* 38-kDa antigen: overproduction in *Escherichia coli*, purification and characterization. *Gene* 117(1): 53–60. August 1992.
5. Rosales-Borjas, D. M., Zambrano-Villa, S., Elinos, M., Kasem, H., Osuna, A., Mancilla, R., and Ortiz-Ortiz, L. Rapid screening test for tuberculosis using a 38-kDa antigen from *Mycobacterium tuberculosis*. *J. Clin. Lab. Anal.* 12 (2): 126–9. 1998.
6. Bassey, E. O. E., Catty, D., Kumararatne, D. S., and Raykundalia, C. Candidate antigens for improved serodiagnosis of tuberculosis. *Tubercle Lung Dis.* 77:136–145. 1996.
7. Kadival, G. V., Chaparas, S. D., and Hussong, D. Characterization of serologic and cell-mediated reactivity of a 38-kDa antigen isolated from *Mycobacterium tuberculosis*. *J. Immunol.* 139(7): 2447–51. October, 1987.
8. Fujiwara, N., Pan, J., Enomoto, K., Terano, Y., Honda, T., and Yano, I. Production and partial characterization of anti-cord factor (trehalose-6,6'-dimycolate) IgG antibody in rabbits recognizing mycolic acid subclasses of *Mycobacterium tuberculosis* or *Mycobacterium avium*. *FEMS Immunol. Med. Microbiol.* 24(2): 141–9. June, 1999.
9. He, H., Oka, S., Han, Y. K., Yamamura, Y., Kusunose, E., Kusunose, M., and Yano, I. Rapid serodiagnosis of human mycobacteriosis by ELISA using cord factor (trehalose-6,6'-dimycolate) purified from *Mycobacterium tuberculosis* as antigen. *FEMS Microbiol. Immunol.* 3(4): 201–4. August, 1991.
10. Enomoto, K., Oka, S., Fujiwara, N., Okamoto, T., Okuda, Y., Maekura, R., Kuroki, T., and Yano, I. Rapid serodiagnosis of *Mycobacterium avium-intracellulare* complex infection by ELISA with cord factor (trehalose 6,6'-dimycolate), and serotyping using the glycopeptidolipid antigen. *Microbiol. Immunol.* 42(10): 689–96. 1998.
11. Chang, Z., Primm, T. P., Jakana, J., Lee, I. H., Serysheva, I., Chiu, W., Gilbert, F., and Quiocho, F. A. *Mycobacterium tuberculosis* 16-kDa antigen (Hsp 16.3) functions as an oligomeric structure in vitro to suppress thermal aggregation. *J. Biol. Chem.* 271:7218–7223. 1996.
12. Cunningham, A. F., and Spreadbury, C. L. Mycobacterial stationary phase induced by low oxygen tension: cell wall thickening and localization of the 16-kilodalton alpha-crystalline homolog. *J. Bacteriol.* 180(4): 801–8. February 1998.

I claim:

1. A method for detecting the presence of at least one antibody to *Mycobacterium tuberculosis* antigens, the antibody present in a sample selected from one or more patient bodily fluids, which comprises the following steps: (a) contacting the sample with a conjugated label having an indicator dye, thereby forming an antibody-conjugated label complex; (b) allowing the antibody-conjugated label complex to migrate along a lateral-flow assay membrane and contact at least one membrane-bound *Mycobacterium tuberculosis* antigen, thereby forming an antigen-antibody complex and causing the indicator dye to precipitate and form a detectable signal; and (c) detecting the signal, whereby the presence of the antibody is determined in the sample by the presence of the signal.

2. The method of claim 1, wherein the one or more bodily fluids is selected from the group consisting of saliva, oral rinse expectorant, oral fluid, gingival crevicular fluid, urine, sweat, tears, blood, serum, stool, gastric fluid, synovial fluid, and phlegm.

3. The method of claim 1, wherein the one or more bodily fluids is saliva or diluted serum.

4. The method of claim 1, further comprising the step of evaluating immunization status of the patient from whom the sample came by comparing the signal or lack thereof with immunizations previously received by the patient and in comparison to a known standard control.

5. The method of claim 1, wherein the antigen specifically binds to Mycobacterium tuberculosis specific antibodies.

6. The method of claim 1, wherein the antigen comprises a mixture of two or more antigens.

7. The method of claim 1, wherein the antigen is selected from the group consisting of 38kDa and 16kDa antigens.

8. The method of claim 1, wherein the membrane has at least a first stripe of the antigen, and a control stripe, the control stripe formed by striping a material that will produce a detectable signal as the sample flows across the control stripe.

9. The method of claim 1, wherein the membrane has a least a first stripe of a first antigen, a second stripe of a second antigen that is different from the first antigen of the first stripe, and a control stripe, the control stripe formed by striping a material that will produce a detectable signal as the sample flows across the control stripe, the second stripe located between the first stripe and the control stripe.

10. The method of claim 9, wherein the second stripe comprises a shared mycobacterial antigen common to all mycobacteria or a mixture of such antigens.

11. An immunoassay kit for detecting at least one antibody to *Mycobacterium tuberculosis* antigens, the antibody present in a sample selected from one or more patient bodily fluids, which comprises: (a) a sample pad, (b) a conjugated label pad, the conjugated label pad having an indicator dye, a portion of the conjugated label pad and a portion of the sample pad forming a first interface, (c) a lateral-flow assay comprising a membrane, a portion of the membrane and a portion of the conjugated label pad forming a second interface, and (d) at least one *Mycobacterium tuberculosis* antigen bound to the membrane, the first interface allowing fluid to flow from the sample pad to the conjugated label pad and contact the indicator dye wherein the antibody present in the sample forms an antibody-conjugated label complex, the second interface allowing fluid to flow from the conjugated label pad to the membrane and to contact the at least one membrane-bound *Mycobacterium tuberculosis* antigen to form to an antigen-antibody complex and cause the indicator dye to precipitate and form a detectable signal.

12. The immunoassay kit of claim 11, wherein the at least one *Mycobacterium tuberculosis* antigen specifically binds to *Mycobacterium tuberculosis* specific antibodies.

13. The immunoassay kit of claim 11, wherein the at least one *Mycobacterium tuberculosis* antigen comprises two or more *Mycobacterium tuberculosis* antigens.

14. The immunoassay kit of claim 11, wherein the at least one *Mycobacterium tuberculosis* antigen is selected from the group consisting of 38 kDa and 16 kDa antigens.

15. The immunoassay kit of claim 11, wherein the membrane has at least a first stripe of the at least one *Mycobacterium tuberculosis* antigen, and a control stripe, the control stripe formed by striping a material that will produce a detectable signal as the sample flows across the control stripe.

16. The immunoassay kit of claim 11, wherein the membrane has a least a first stripe of a first antigen, a second stripe of a second antigen that is different from the first antigen of the first stripe, and a control stripe, the control stripe formed by striping a material that will produce a detectable signal as the sample flows across the control stripe, the second stripe located between the first stripe and the control stripe.

17. The immunoassay kit of claim 16, wherein the second stripe comprises a shared mycobacterial antigen common to all mycobacteria or a mixture of such antigens.

18. The immunoassay kit of claim 11, wherein the conjugated label pad comprises Protein A.

19. The immunoassay kit of claim 18, wherein the conjugated label comprises colloidal gold.

20. The method of claim 1, wherein the conjugated label comprises Protein A.

21. The method of claim 20, wherein the conjugated label comprises colloidal gold.

22. The method of claim 1, wherein the at least one membrane-bound *Mycobacterium tuberculosis* antigen is selected from the group consisting of purified protein derivative, natural and recombinant proteins selected from the group consisting of 38 kDa, 16 kDa, ESAT-6, MPT-63, TB23 HYT6, F29.47, 21-2H3, and MPT40 antigens or a mixture thereof.

23. The method of claim 9, wherein the first stripe comprises a latent *Mycobacterium tuberculosis* antigen, and the second stripe comprises an active *Mycobacterium tuberculosis* antigen.

24. The method of claim 10, wherein the second stripe comprises a mixture of shared common mycobacterial antigens selected from the group consisting of P32 of *M bovis*, 65 kDa BCG antigen, 64 kDa BOG antigen, MPB57, BCG-a, and LAM.

25. The method of claim 1, wherein the antigen is a recombinant antigen.

26. The immunoassay kit of claim 11, wherein the at least one *Mycobacterium tuberculosis* antigen bound to the membrane is selected from the group consisting of purified protein derivative, natural and recombinant proteins selected from the group consisting of 38 kDa, 16 kDa, ESAT-6, MPT-63, TB23 HYT6, F29.47, 21-2H3, and MPT40 antigens or a mixture thereof.

27. The immunoassay kit of claim 16, wherein the first stripe comprises a latent *Mycobacterium tuberculosis* antigen, and the second swipe comprises an active *Mycobacterium tuberculosis* antigen.

28. The immunoassay kit of claim 17, wherein the second stripe comprises a mixture of shared common mycobacterial antigens selected from the group consisting of P32 of *M bovis*, 65 kDa BCG antigen, 64 kDa BCG antigen, MPB57, BCG-a, and LAM.

29. The immunoassay kit of claim 11, wherein the antigen is a recombinant antigen.

* * * * *